(12) United States Patent
Schubert et al.

(10) Patent No.: US 9,146,201 B2
(45) Date of Patent: Sep. 29, 2015

(54) CONVERTIBLE SCAN PANEL FOR X-RAY INSPECTION

(71) Applicant: American Science and Engineering, Inc., Billerica, MA (US)

(72) Inventors: Jeffrey Schubert, Somerville, MA (US); Jeffrey M. Denker, Woburn, MA (US); Jason Toppan, Burlington, MA (US); Michael Chesna, Saugus, MA (US); Richard Mastronardi, Medfield, MA (US); Robyn Smith, Bolton, MA (US); Richard Schueller, Chemsford, MA (US); Jeffrey Illig, Verona, WI (US)

(73) Assignee: American Science and Engineering, Inc., Billerica, MA (US)

( * ) Notice: Subject to any disclaimer, the term of this patent is extended or adjusted under 35 U.S.C. 154(b) by 191 days.

(21) Appl. No.: 13/748,036

(22) Filed: Jan. 23, 2013

(65) Prior Publication Data

US 2013/0202089 A1 Aug. 8, 2013

Related U.S. Application Data

(60) Provisional application No. 61/593,978, filed on Feb. 2, 2012.

(51) Int. Cl.
*G01N 23/203* (2006.01)
*G01N 23/04* (2006.01)
(Continued)

(52) U.S. Cl.
CPC ............ *G01N 23/203* (2013.01); *G01V 5/0025* (2013.01); *G01N 23/04* (2013.01); *G01N 23/201* (2013.01); *G01V 5/0008* (2013.01)

(58) Field of Classification Search
CPC ... G01N 23/201; G01N 23/203; G01N 23/04; G01N 23/20; G01V 5/0008; G01V 5/0016; G01V 5/0025; G01V 5/0075; B60J 1/00

USPC ........ 378/57, 64, 70, 86, 98.8, 146, 156, 157, 378/161
See application file for complete search history.

(56) References Cited

U.S. PATENT DOCUMENTS 2,992,851 A * 7/1961 Bela .................................. 49/223
3,165,658 A * 1/1965 Zunick ........................... 378/141
(Continued)

FOREIGN PATENT DOCUMENTS

| WO | WO 00/33060 A2 | 6/2000 | ............ G01N 23/20 |
|---|---|---|---|
| WO | WO 2011/008718 A1 | 1/2011 | ............... H05G 1/02 |
| WO | WO 2011/011583 A1 | 1/2011 | ............... A61B 6/00 |

OTHER PUBLICATIONS

Nikl, Scintillation detectors for x-rays, Meas. Sci. Technol., Apr. 2006, vol. 17. p. R38.*

(Continued)

*Primary Examiner* — Irakli Kiknadze
*Assistant Examiner* — Julio M Duarte-Carvajalino
(74) *Attorney, Agent, or Firm* — Sunstein Kann Murphy & Timbers LLP

(57) ABSTRACT

An x-ray inspection system using backscatter of an x-ray beam emitted through a scan panel contiguous with, but of a material distinct from, an enclosure that contains an x-ray source by which the x-ray beam is generated. The scan panel is contoured in such a manner as to be visibly blended with a shape characterizing the enclosure. In some embodiments, the beam traverses multiple scan panels, where one or more of the scan panels may be selected for beam filtration properties. The scan panel may be disposed interior to a sliding door, and may be structured to serve as a scatter shield.

14 Claims, 2 Drawing Sheets

(51) Int. Cl.
*G01N 23/201* (2006.01)
*G01V 5/00* (2006.01)

(56) References Cited

U.S. PATENT DOCUMENTS

| | | | | |
|---|---|---|---|---|
| 4,075,526 | A | * | 2/1978 | Grubis ........................ 378/124 |
| 5,077,771 | A | * | 12/1991 | Skillicorn et al. ............ 378/102 |
| 5,692,028 | A | | 11/1997 | Geus et al. ..................... 378/57 |
| 5,764,683 | A | | 6/1998 | Swift et al. .................... 378/57 |
| 6,249,567 | B1 | * | 6/2001 | Rothschild et al. ............. 378/88 |
| 6,282,260 | B1 | * | 8/2001 | Grodzins ....................... 378/87 |
| 7,099,434 | B2 | | 8/2006 | Adams et al. .................. 378/57 |
| 7,218,704 | B1 | | 5/2007 | Adams et al. .................. 378/57 |
| 7,505,556 | B2 | | 3/2009 | Chalmers et al. ............... 378/57 |
| 2007/0172032 | A1 | * | 7/2007 | Lowman ...................... 378/198 |
| 2009/0257555 | A1 | * | 10/2009 | Chalmers et al. ............... 378/57 |

OTHER PUBLICATIONS

Stodolsky et al., Lightweight materials in the light-duty passenger vehicle market: their market penetration potential and impacts, Mar. 1995, Center for Transportation Research Argonne National Laboratory, p. 3, 6.*

Martin, The importance of radiation quality for optimisation in Radiology, Apr. 2007, Biomed Imaging Intery J., vol. 3, No. 2, p. 2, 3, 5, 8, 9, 13.*

Baron et al., Beryllium and aluminium refractive collimators for synchrotron radiation, Sep. 1999, J. Synchrotron Rad. vol. 6, p. 953, 954.*

Ahn, Jae Yul Authorized officer Korean Intellectual Property Office International Search Report and Written Opinion of the International Searching Authority—Application No. PCT/US2013/022715, dated May 15, 2013 (10 pages).

* cited by examiner

CONVERTIBLE SCAN PANEL FOR X-RAY INSPECTION

The present application claims the priority of U.S. Provisional Application Ser. No. 61/593,978, filed Feb. 2, 2012, and incorporated herein by reference.

TECHNICAL FIELD

The present invention relates to methods and apparatus for coupling penetrating radiation out of, and/or into, an enclosure for purposes of inspecting objects disposed outside the enclosure.

BACKGROUND ART

Materials within containers not readily susceptible to visual scrutiny, or, alternatively, materials that may be carried on the person of a human or on another animate subject, are routinely inspected by measurement of x-rays scattered by the materials from an irradiating x-ray beam. The characteristics of a material which might be the object of non-invasive inspection and which lend themselves to detection using the device and method taught by the invention include, but are not limited to, electron density, atomic number, mass density, linear dimensions and shape. These characteristics are unveiled by taking advantage of the various physical processes by which penetrating radiation interacts with matter. Additionally, scattered penetrating radiation may be used for imaging contents concealed within a vehicle or other container. Scattering in the backward direction may be referred to as backscatter, and is particularly implicated in the teachings of the present invention.

Penetrating radiation refers to electromagnetic radiation (or radiation of massive particles, such as neutrons) of sufficient energy per particle to penetrate materials of interest to a substantial and useful degree and include x-rays and more energetic forms of radiation. The interaction of such radiation with matter can generally be categorized as either scattering or absorption processes. Both types of process remove x-ray photons from a collimated (i.e., directional) beam; scattering processes do so by deflecting photons into new directions (usually with loss of energy), while absorption processes simply remove photons from the beam. As used herein, the term "x-ray" may be used as exemplary of penetrating radiation generally.

Description of the rudiments of various mobile inspection systems may be found in U.S. Pat. No. 5,764,683, issued Jun. 9, 1998, and in U.S. Pat. No. 7,099,434, issued Aug. 29, 2006, both of which incorporated herein by reference. As used in this description and in any appended claims, the term "source" is used in a broad sense to encompass the entirety of the apparatus used to generate a beam of penetrating radiation that is used to irradiate the object under inspection. The source is taken to include the generator of penetrating radiation (the "source", in the narrow sense) which may include an x-ray tube or a radio-isotope. It is, furthermore, to be understood that the term "source" as used herein and in any appended claims, and as designated generally by numeral 30 in the drawings, refers to the entirety of the apparatus used to generate beam 24, and may have internal components that include, without limitation, apertures, choppers, collimators, etc.

Scatter imaging in which the x-rays scattered by a material (typically in a generally backward direction) are employed offers several unique inspection capabilities and operational features. Scatter imaging allows images to be obtained even when the imaged object is accessible from only one side. Moreover, since the scatter signal falls off quite rapidly with increasing depth into the object, backscatter images effectively represent a "slice" of the object characteristic of the side nearest to the x-ray source, thereby reducing problems of image clutter that may confound transmission images. The Compton effect, which dominates x-ray scatter in the energy range typically employed in accordance with the present invention, dominates the interaction of x-rays with dense low-atomic-number (low-Z) materials. Narcotic drugs tend to produce the bright signatures in a backscatter image, as do organic explosives, making backscatter imaging a useful imaging modality for bomb or drug detection. Finally, alignment requirements of the x-ray beam with detectors or collimation devices are less exacting than for transmission imaging thereby enabling rapid deployment in a wide range of inspection scenarios.

Flying-spot technology makes possible the acquisition of images using detectors specifically positioned to collect the scattered x-rays. In a typical flying-spot system, a thin "pencil beam" of x-rays is rapidly and repetitively swept through a source-centered track of beam paths that are arranged to intercept the object under inspection. At the same time, the inspection system moves relative to the inspected object at a substantially constant, slower speed along a path perpendicular to the track of the swept pencil beam. (It is to be understood that whether the source or the object moves relative to a local rest frame is immaterial to the present invention as claimed.) In this way, the pencil beam is made to traverse the object in point-by-point raster fashion, and the entire object is scanned as it passes through the fan plane over a period ranging from a few seconds to a few minutes depending upon the length of the object and the relative velocity of the object and the source.

FIG. 1 depicts a prior art mobile backscatter inspection system, such as described in U.S. Pat. No. 7,099,434, in which context embodiments of the present invention are advantageously applied. Backscatter detectors 100 are mounted on a mobile platform 10, or conveyance, typically capable of road travel, that traverses a large object to be inspected such as a vehicle or a cargo container 12. Conveyance 10 is characterized by an enclosure 14, here, the skin of a van, shown, in cutaway view, to enable depiction of other components of an inspection system. The conveyance can have many alternate embodiments, including but not limited to gasoline, diesel, electric, propane, battery, fuel-cell, or hydrogen-powered motor vehicles (including vans, trucks, or similar), tracked vehicles, sleds, trailers, cranes, or other equipment that can be put into motion, preferably self-propelled, but also including vehicles tethered and pulled such as under electric power.

Contained within enclosure 14 of conveyance 10 is a source 30 including x-ray tube 32 (shown in FIG. 2) and chopper 34. Rotating hoop 34, with aperture 38, emits a pencil beam 24 (also referred to, herein, as an "outgoing beam," or "illuminating x-ray beam," or "primary beam"), thereby enabling inspection of object 12.

Various means are known in the art for mechanically or electronically sweeping a beam of penetrating radiation, including, for example, the rotating chopper wheel 34 depicted in FIG. 2, or electronic scanning as described in detail, for example, in U.S. Pat. No. 6,421,420, issued Jul. 16, 2002, which is incorporated herein by reference. In embodiments employing a mechanical rotating chopper wheel 34, as the chopper wheel rotates in the direction of arrow 22, outgoing beam 24 of penetrating radiation emitted from the target of x-ray tube 32 passes successively through a plurality of channels.

Detectors 100 detect penetrating radiation from source 30 that has interacted with, and scattered from, contents of the inspected object 12, are carried by conveyance 10 and are typically enclosed within enclosing body 14 and concealed from view from outside the conveyance. They may also be carried outside the conveyance for particular applications within the scope of the present invention, as taught in U.S. Pat. No. 5,764,683. Detectors 100 are electrically coupled to processor 40, which receives and processes scatter signals, to render images of inspected object 12 and its contents, and/or to compute material characteristics of the contents of inspected object 12.

SUMMARY OF EMBODIMENTS OF THE INVENTION

In accordance with embodiments of the present invention, an inspection system is provided for inspection, by backscatter, of objects disposed outside an enclosure. The inspection system has a source for generating a beam of penetrating radiation, where the source is disposed within an enclosure. A portion of the enclosure, traversed by the beam, constitutes a scan panel including a material distinct from material comprising another portion of the enclosure not traversed by the penetrating radiation, and contoured in such a manner as to be visibly blended with a shape characterizing the enclosure. The inspection system also has at least one scatter detector for receiving penetrating radiation scattered from the beam of penetrating radiation by the inspected object.

In some, but not all, embodiments of the invention, the material and/or the thickness of the scan panel may be optimized with respect to contrast-to-noise ratio of one or more selected materials within the inspected object.

In accordance with further embodiments of the invention, a second scan panel may be interposed between the inspected object and the scatter detector (or detectors). The first scan panel may be characterized by an effective atomic number less than 26, as may the second, and either (or both) may be selected for beam filtration properties.

In accordance with yet further embodiments of the invention, a scan panel may be covered by a door during non-operational periods of the inspection system. The scan panel may be interchangeable with a door, or may be disposed interior to a sliding door.

In alternate embodiments of the invention, the scan panel may have either an interior, or an exterior, scatter shield, or both. The enclosure may be borne on a conveyance, and, in other embodiments, the enclosure may support weight of objects undergoing inspection.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS OF THE INVENTION

Definitions

As used herein and in any appended claims, the term "beam" refers to a flux of particles (including, particularly, photons such as X-rays or gamma-rays) having a predominant direction referred to as the direction of the beam. Any plane containing the direction of the beam may be referred to as a plane of the beam.

The term "image" shall refer to any multidimensional representation, whether in tangible or otherwise perceptible form, or otherwise, whereby a value of some characteristic (such as fractional transmitted intensity through a column of an inspected object traversed by an incident beam, in the case of x-ray transmission imaging) is associated with each of a plurality of locations (or, vectors in a Euclidean space, typically $\mathcal{R}^2$) corresponding to dimensional coordinates of an object in physical space, though not necessarily mapped one-to-one thereonto. An image may comprise an array of numbers in a computer memory or holographic medium. Similarly, "imaging" refers to the rendering of a stated physical characteristic in terms of one or more images.

As used herein, and in any appended claims, the term "penetration contrast" shall refer to any measure of the relative signal difference between an organic target behind some thickness of steel (or other fiducial attenuating material), and the adjacent steel surrounding the organic object in the image.

Contrast-to-Noise ratio, as used herein, shall be defined with respect to a particular material (such as a material sought within an inspected object, for example) and shall have the following definition:

$$CNR \equiv \frac{S_{mat} - S_{bgnd}}{\sigma_{mat}},$$

where $S_{mat}$ is a backscatter signal intensity derived by measurement (with suitable averaging) of a specified target material through a scan panel, $S_{b\,gnd}$ is a corresponding backscatter background measured under the same conditions, but absent the presence of the specified target material, and $\sigma^{mat}$ is the standard deviation of scatter in the measurement of the backscatter signal from the specified target under specified conditions of signal acquisition duration, etc.

Figure 1:
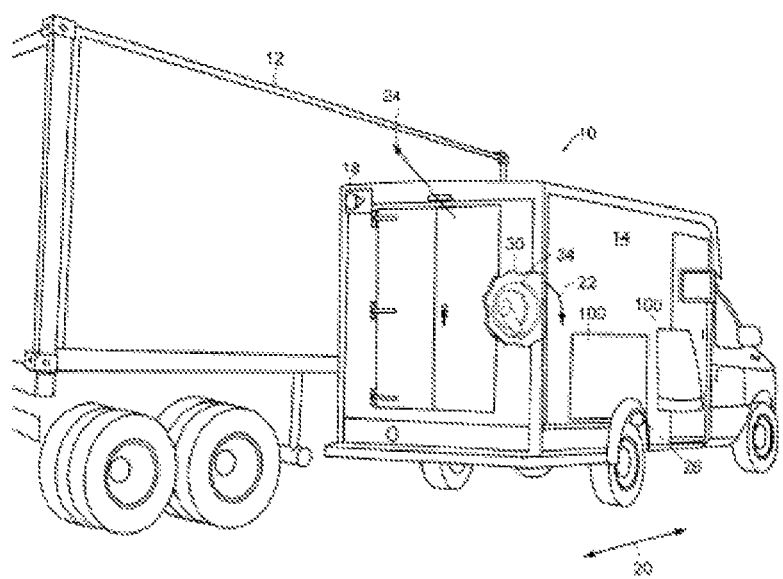
FIG. 1 is a perspective view of a prior art mobile x-ray backscatter inspection system.
Figure 2:
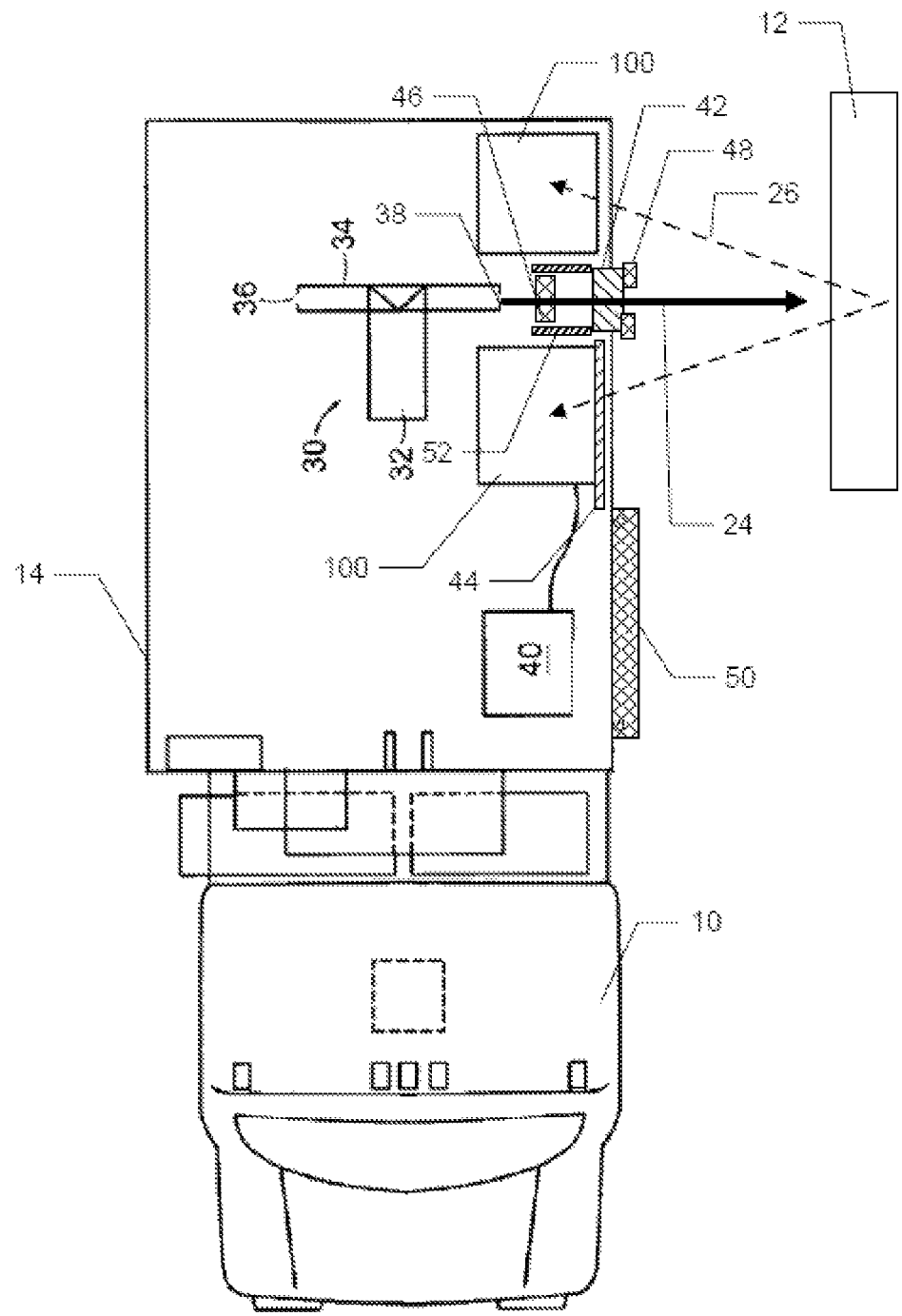
FIG. 2 is a schematic representation of an inspection vehicle, in accordance with embodiments of the present invention, depicting structural elements for transmission and filtration of an illuminating beam and scattered radiation.

Embodiments of the present invention are now described with reference to FIG. 2. Contained within enclosure 14 of conveyance 10 is source 30, including x-ray tube 32 and chopper 34, with aperture 38, which emits a pencil beam 24, thereby enabling inspection of object 12. Scattered x-rays 26 impinge upon scatter detectors 100 giving rise to backscatter signals processed by processor 40.

DEFINITION

For a backscatter imaging system located within an enclosure such as enclosure 14 (which may be the coach of conveyance 10 but need not be, within the scope of the present invention), the term "scan panel" shall refer to any material contiguous with, or covering, a plane containing any portion of enclosure 14 that is traversed by either outgoing beam 24 and/or by scattered radiation 26 passing from inspected object 12 to one or more scatter detector 100. Scan panel 42, interposed within outgoing beam 24, and detector scan panel 44, interposed between inspected object 12 and scatter detector 100, are shown in FIG. 2. Scan panels 42 and 44 may be constituted by a single scan panel, within the scope of the present invention.

In the case of an imaging system built into a vehicle 10, such as a panel van, with a body that is typically made of steel, a vehicle door, or other portion of enclosure 14 may be removed and replaced with suitably x-ray transparent material to serve as the scan panel.

As used herein, the term "suitably x-ray transparent" refers to a material exhibiting attenuation of less than 90%, meaning that at least 10% of the beam, over an energy range of interest, survives traversal of the "suitably x-ray transparent" medium. A scan panel preferably removes no more than 30% of the beam, and, in preferred embodiments of the invention, the beam is characterized by an x-ray bremsstrahlung spectrum having an endpoint energy of 225 keV. A preferred "suitably x-ray transparent material" for use in accordance with the present invention is any composite structure of fiber-reinforced polymer adhered to, or encapsulating, a cellular matrix (e.g. honeycomb or polymer foam). This material is preferred because of its formability, rigidity, tensile strength, and its substantial x-ray transparency above 30 keV for thicknesses less than 1 cm. Other materials or composite structures of low effective atomic number Z (which, by definition, for purposes of the present patent application only, refers to $Z_{\mathit{eff}}$<26) may also be selected as suitably x-ray transparent materials as a matter of design choice under distinct circumstances.

Optimization with Respect to Contrast-to-Noise Ratio

In order to optimize selection of a candidate scan panel material with respect CNR, the backscatter signal $S_{mat}$ is measured from the same uniform scattering material using, in succession, each of a set of candidate scan panels. The scan panel for which the CNR is greatest for the scattering material concerned, where CNR is as defined above, is chosen as the CNR-optimized scan panel. Both the scan panel material and its thickness may be optimized in this manner.

Integration of Beam Filter and Scan Panel

A beam filter 46 may be interposed within illuminating x-ray beam 24 for controlling the dose, and shaping the spectrum, of beam 24. Scan panel 42 (between source 30 and inspected object 12) and scan panel 44 (between inspected object 12 and detector 100) may serve as structural windows in front of both the beam and detectors. Ideal structural materials often contain high-Z elements that further filter the beam. Scan panel 42 may replace part or all of the functionality of beam filter 46. If the panel is too thick, forward-scattered x-rays from the panel could fog the image and degrade resolution, however, this may be mitigated with an external scatter shield 48 which collimates beam 24 after traversing enclosure 14. If panel 42 is thin enough (namely, having an attenuation-length product less than that of 2-mm of Aluminum for a 225 keV endpoint bremsstrahlung spectrum), no external scatter shield 48 is required.

Beam Filter in Front of Detector and its Integration with a Scan Panel

In certain circumstances, spectral filtration in front of the detector 100 may be tantamount to filtration of the primary beam, although to maximize flux while minimizing dose, it is usually preferable to place all needed filtration in the primary beam, and as little as possible in front of the detector. In some cases, such as multiple-energy backscatter, or if sufficient flux exists and/or a lower dose than is required, and if an increase in penetration-contrast is sought and it is inconvenient to adjust the filtration in primary beam, then added filtration might be placed in front of the detector. Such filtration may be achieved, in whole or in part, from the scan panel. In such a case, the panel is preferably composed of moderate-Z materials such as aluminum (Z=13) or PVC plastic (containing chlorine, Z=17); however, any element on the periodic table can be used, provided that its thickness is proportionate to its attenuation properties. Examples are 1.5 mm of aluminum or 3-4 mm of Kydex®, an alloy of acrylic and PVC.

Convertible Covert-to-Non-Covert-Mode Inspection

In accordance with embodiments of the present invention, a functional door may be fashioned out of aluminum or plastic, optionally with a steel framework at the edges, and the door may be opened to reveal a standard aluminum scan panel, or a thinner plastic panel, for better image flux. In those embodiments, the van has two modes: Covert or Highest Quality Imaging. Covert-mode achieves its covertness, relative to an embodiment with a plastic faux-door, for example, because no compromises are made to the door structure to improve imaging. High-Quality mode affords higher-quality imaging than available with a steel door by virtue of a very thin (<20 mil) aluminum or polymer scan panel, for higher SNR, or by virtue of a spectrally optimized scan panel, as discussed above. When the van is on the highway or being stored outside, a door 50 is closed, so image quality does not need to be compromised for structural integrity, weather-proofing, etc.

Imaging System Behind Sliding Door

A simpler variation on embodiments with convertible covert-to-non-covert doors, is a system, in accordance with an alternate embodiment of the invention, that only has High-Quality Imaging mode, but can be covert when not imaging. In this embodiment, van 10 can drive up to and away from a target 12 covertly, but a door 50 must be opened for x-ray scanning. In this case the standard steel door could be used with no modification. A simple, flat, scan panel 42 is mounted directly behind door 50 and needs only to be minimally weather tight, or not weather tight at all. In certain embodiments, there may be no scan panel at all, as where weather, sand, dirt, or splashing liquid hazards need not be considered. A more ambitious variation on this method camouflages an optimized scan panel 42, for example by making it look like the side of a stack of cardboard boxes, or like some other object that one might plausibly see inside a delivery van when the side door is open. An automatic opening/closing mechanism may be built in to allow the operator to more rapidly initiate a scan (and to quickly leave the area after a scan).

In some embodiments of the invention, a vehicle's factory body or door panel is replaced with a scan panel 42 that maintains the original aesthetics, and/or is indiscernible from the original. In preferred embodiments of the invention, a backscatter x-ray system mounted in an enclosure 14 employs a low-Z "scan panel" 42 in the path of x-ray beam 24 and in front of backscatter detectors 100. If the system is mounted in or on a vehicle 10, the scan panel 42 is weather tight. If the system must be covert, scan panel 42 does not alter the appearance of the vehicle. Unibody vehicles, like a common panel van, pose a problem in that the sides of the vehicle are made of steel and are not suitable for the scan panel 42. A custom coach for a box truck can be made of aluminum or other low-Z materials, but box trucks are not as effective for covert applications as a panel van, and are also less desirable if there are motivations to create an aesthetic product. For vehicles with a side door (as is common on panel vans) the door can be removed and replaced with a purpose built scan panel. Removing a single part poses a minimum risk of compromising the mechanical integrity of the vehicle and presents a minimum of engineering issues that affect the vehicle. A scan panel can be fabricated from a variety of materials to have the same shape as the door it replaced. Materials, however, can be selected from those that are suitably transparent to x-rays.

Contour Smoothing

Curves, contours, or other geometric features in scan panel 42 or 44 have the potential to create both bright and dark bands in the backscatter image, whether operated in a covert or non-covert mode. Bands are created when there are variations in the thickness of the material in the region 42 that the primary pencil beam passes through. A local 'thick region' both scatters more and attenuates more of the primary beam than the adjacent thinner regions. If the added scatter gets into the backscatter detectors, it creates a bright band. The attenuation creates a dark band depending in part on nature of the object being imaged. The proportion of bright-to-dark influence on the total signal is a function both of the composition of scan panel 42 and the nature of what is being imaged. In general the bright bands are more noticeable, and bright bands can be mitigated through each of the following embodiments of the present invention:

An internal scatter shield 52 conforms to the shape of the scan panel, to block scatter off of the scan panel from reaching the detectors.

Both bright and dark bands can be mitigated or eliminated by modifying the shape of the scan panel through use of the following:

a. Creating a smooth region in the plane of the beam. The smooth region can be blended with the rest of the overall shape of the panel to maintain aesthetics or covertness. For example, on some chasses, the most severe image artifacts are caused by the contours at the top and bottom of the faux-window. The sides of this panel van, like many panel vans, are contoured to create the shape of a large side window, even though the entire door is a sheet of metal. A faux-mullion can be added to the panel to divide the large faux-window into two faux-windows. This can be styled to look every bit as normal as the original faux-window design. An external observer would need to inspect both the imaging and non-imaging side of the van to detect any asymmetry, and even then it would not be obvious that this is not an intentional styling of a normal panel van.

b. In the same situation described above, the "faux window" or other problem causing feature could simply be removed from the design, leaving a smooth featureless region in the scan panel. The elimination of such features will also serve to remove cost from the fabrication of the covert/aesthetic scan panel.

All offensive contours may simply be smoothed in the region of the beam plane, to create a balance of minimizing image impact while minimizing modification to the aesthetic design.

The selection of features from among the forgoing is a design choice that depends upon the desired balance of covert and/or aesthetic features vs. desire for smooth, featureless scan panel for ideal image quality.

While concepts in accordance with the present invention have been described herein, without limitation, with reference to enclosure 14 mounted on vehicle 10 of a mobile inspection system, it is to be understood that many aspects of various embodiments of the present invention are advantageously used in a weight-bearing scan panel of a bottom-up backscatter parcel scanner, as described, for example, in U.S. Pat. No. 5,483,569 (to Annis), which is incorporated herein by reference. Moreover, concepts in accordance with embodiments of the present invention may be applied advantageously to any backscatter system with a protective panel in front of the detectors and beam exit, whatever its geometrical orientation, and without regard to whether or not the scan panel surface is weight-bearing.

Where examples presented herein involve specific combinations of method acts or system elements, it should be understood that those acts and those elements may be combined in other ways to accomplish the same objective of providing multiple x-ray fan beams from a single source. Additionally, single device features may fulfill the requirements of separately recited elements of a claim. The embodiments of the invention described herein are intended to be merely exemplary; variations and modifications will be apparent to those skilled in the art. All such variations and modifications are intended to be within the scope of the present invention as defined in any appended claims.

What is claimed is:

1. An inspection system for inspecting an inspected object with backscattered penetrating radiation, the inspection system comprising:
  a. a source for generating a pencil beam of x-rays, the source disposed within an enclosure during operation of the inspection system, the enclosure borne on a conveyance;
  b. a portion of the enclosure traversed by the pencil beam of x-rays, the portion of the enclosure constituting a first scan panel, characterized by a thickness and including a material distinct from material comprising another portion of the enclosure not traversed by the pencil beam of x-rays, and contoured in such a manner as to be visibly blended with a shape characterizing the enclosure; and
  c. at least one scatter detector for receiving x-ray radiation scattered from the pencil beam of x-rays by the inspected object.

2. An inspection system in accordance with claim 1, wherein at least one of the material and thickness of the first scan panel is optimized with respect to contrast-to-noise ratio of a selected material within the inspected object.

3. An inspection system in accordance with claim 1, wherein the first scan panel is characterized by an effective atomic number less than 26.

4. An inspection system in accordance with claim 1, wherein the first scan panel is selected for beam filtration properties.

5. An inspection system in accordance with claim 1, wherein the first scan panel is interchangeable with a door.

6. An inspection system in accordance with claim 2, wherein at least one of the first scan panel and the second scan panel is interchangeable with a door.

7. An inspection system in accordance with claim 1, wherein the first scan panel is disposed interior to a sliding door.

8. An inspection system in accordance with claim 2, wherein at least one of the first scan panel and the second scan panel is disposed interior to a sliding door.

9. An inspection system in accordance with claim 1, wherein the first scan panel comprises an exterior scatter shield.

10. An inspection system in accordance with claim 1, wherein the first scan panel comprises an interior scatter shield.

11. An inspection system in accordance with claim 1, wherein the enclosure supports weight of objects undergoing inspection.

12. An inspection system for inspecting an inspected object with backscattered penetrating radiation, the inspection system comprising:

a. a source for generating a pencil beam of x-rays, the source disposed within an enclosure during operation of the inspection system;
b. a portion of the enclosure traversed by the pencil beam of x-rays, the portion of the enclosure constituting a first scan panel, characterized by a thickness and including a material distinct from material comprising another portion of the enclosure not traversed by the pencil beam of x-rays, and contoured in such a manner as to be visibly blended with a shape characterizing the enclosure;
c. at least one scatter detector for receiving x-ray radiation scattered from the beam of penetrating radiation by the inspected object; and
d. a second scan panel interposed between the inspected object and the at least one scatter detector.

13. An inspection system in accordance with claim 12, wherein the second scan panel is characterized by an effective atomic number less than 26.

14. An inspection system for inspecting an inspected object with backscattered penetrating radiation, the inspection system comprising:
a. a source for generating a pencil beam of x-rays, the source disposed within an enclosure during operation of the inspection system;
b. a portion of the enclosure traversed by the pencil beam of x-rays, the portion of the enclosure constituting a first scan panel, characterized by a thickness and including a material distinct from material comprising another portion of the enclosure not traversed by the pencil beam of x-rays, and contoured in such a manner as to be visibly blended with a shape characterizing the enclosure; and
c. at least one scatter detector for receiving x-ray radiation scattered from the beam of penetrating radiation by the inspected object;

wherein the first scan panel is covered by a door during non-operational periods of the inspection system.

* * * * *